United States Patent
Lepage et al.

(10) Patent No.: US 7,505,859 B2
(45) Date of Patent: Mar. 17, 2009

(54) METHOD AND ALGORITHMS FOR INSPECTION OF LONGITUDINAL DEFECTS IN AN EDDY CURRENT INSPECTION SYSTEM

(75) Inventors: Benoit Lepage, Quebec (CA); Patrick Vachon, Quebec (CA)

(73) Assignee: Olympus NDT, Waltham, MA (US)

( * ) Notice: Subject to any disclaimer, the term of this patent is extended or adjusted under 35 U.S.C. 154(b) by 0 days.

(21) Appl. No.: 11/696,918

(22) Filed: Apr. 5, 2007

(65) Prior Publication Data

US 2008/0246468 A1    Oct. 9, 2008

(51) Int. Cl.
*G06F 19/00* (2006.01)
(52) U.S. Cl. ......................... 702/85; 324/225
(58) Field of Classification Search ............. 702/85, 702/69, 76, 77, 182–185, 188; 324/225, 324/227, 232, 242; 73/618, 633
See application file for complete search history.

(56) References Cited

U.S. PATENT DOCUMENTS

| | | | |
|---|---|---|---|
| 3,152,302 A | 10/1964 | Allen et al. | 324/34 |
| 3,906,357 A | 9/1975 | Runshang | 324/37 |
| 4,203,069 A | 5/1980 | Davis | 324/220 |
| 4,218,651 A | 8/1980 | Ivy | 324/227 |
| 4,673,879 A | 6/1987 | Harris et al. | 324/240 |
| 4,965,519 A | 10/1990 | Törnblom | 324/225 |
| 5,371,462 A | 12/1994 | Hedengren et al. | 324/225 |
| 6,220,099 B1 * | 4/2001 | Marti et al. | 73/633 |
| 2007/0084288 A1 * | 4/2007 | Thomas | 73/627 |

* cited by examiner

*Primary Examiner*—Edward Raymond
(74) *Attorney, Agent, or Firm*—Ostrolenk, Faber, Gerb & Soffen LLP

(57) ABSTRACT

A collection of data processing algorithms which, used in concert, are suitable for use in place of a high pass filter stage in an eddy current inspection system and provide for a system optimized to inspect test pieces for elongated defects running parallel to the scan axis. The algorithms use mathematical techniques to eliminate baseline impedance offset between test pieces, correct for offset drift during a scan, and allow for system balancing using only a set of test pieces of unknown quality.

11 Claims, 10 Drawing Sheets

The BIOC Algorithm is defined as:

$$Y_n = X_n + C_n$$

WHERE:
$X_n$ is the raw input data value
$C_n$ is the Correction Factor, defined as:

$$C_n = \text{SLOPE} * \text{ADJ}_n$$

WHERE:
SLOPE is a constant value defined by the user[1]
$\text{ADJ}_n$ is the Adjustment Index defined as:

$$\begin{cases} \text{if } n = 0 \cap X_n \geq 0, & \text{ADJ}_n = -1 \\ \text{if } n = 0 \cap X_n < 0, & \text{ADJ}_n = 1 \\ \text{if } n > 0 \cap |Y_{n-1}| \geq \text{THRESHOLD}, & \text{ADJ}_n = \text{ADJ}_{n-1} \\ \text{if } n > 0 \cap |Y_{n-1}| < \text{THRESHOLD} \cap Y_{n-1} \geq 0, & \text{ADJ}_n = \text{ADJ}_{n-1} - 1 \\ \text{if } n > 0 \cap |Y_{n-1}| < \text{THRESHOLD} \cap Y_{n-1} < 0, & \text{ADJ}_n = \text{ADJ}_{n-1} + 1 \end{cases}$$

WHERE:
THRESHOLD is a constant value defined by the user[2]

[1] A value for SLOPE is typically chosen to be twice the average slope of the anticipated offset drift.

[2] A value for THRESHOLD is typically chosen to be just less than the alarm gate setting.

FIG. 5B

METHOD AND ALGORITHMS FOR INSPECTION OF LONGITUDINAL DEFECTS IN AN EDDY CURRENT INSPECTION SYSTEM

BACKGROUND OF THE INVENTION

The present invention relates to the inspection of components employing eddy current techniques, and more particularly, to the processing of signals from an eddy current probe array.

Any discussion of the related art throughout the specification should in no way be considered as an admission that such art is widely known or forms part of the common general knowledge in the field.

Eddy current inspection is commonly used to detect flaws in manufactured components, such as tubes or billets. An inspection coil, typically referred to as an eddy current probe, is positioned near a piece to be inspected and driven with high frequency alternating electrical currents which, in turn, create an alternating magnetic field near the surface of the test piece. This magnetic field induces eddy currents in the conductive surface of the test piece which are sensed and measured by the eddy current probe. If a flaw or defect is present on the surface of the test piece, the flow of eddy currents will be altered, and this change will be readily detected by the eddy current probe. The amplitude and position of these current changes can then be analyzed and recorded, for example through visual inspection by a test operator or processed through an automated alarm algorithm, to determine the size and location of the defect or flaw. Eddy current array systems comprise of a plurality of inspection coils arranged in such a way as to be conducive to a particular inspection task.

Both single element and array probe eddy current inspection systems require probe balancing prior to scanning to ensure that flaw detection and sizing is accurate. Certain unavoidable variations, such as exact probe placement, manufacturing differences between coil assemblies, or environmental variables, make it impossible to predict the exact impedance readings sensed by the coil or coils in an eddy current probe for a given surface. Balancing is a process by which a reference reading for each coil in the eddy current probe is measured and recorded. This reference value is then subtracted from all subsequent measurements sensed by each coil, pulling the baseline, or null point, of each impedance reading to zero.

Complicating the issue of coil balancing in an eddy current probe is unit to unit variation among test pieces. Certain factors, such as metallurgic discrepancies or geometric variations, will affect the impedance of each test piece, and therefore result in different eddy currents for the same magnetic field. As a result, the baseline measurement will shift from test piece to test piece. This can be problematic for accurately detecting and sizing flaws.

A second complication concerning probe balancing in eddy current systems is what is typically referred to as baseline drift. In this case, metallurgic, geometric, or temperature variations, for example, along the scan path of a single test piece cause the baseline impedance reading seen by each eddy current coil in the probe to drift within the impedance plane. While these impedance variations are typically anticipated by and within the tolerance of the manufacturing process, they can limit the sensitivity of the eddy current inspection system and impede the detection of small defects.

In prior art systems, these baseline shifts—both those resulting from test piece variation and those resulting from baseline drift—were eliminated with the use of a high pass filter, which would eliminate the DC component of the measured eddy current signals, thus moving the null point of the test piece to zero regardless of the inherent impedance of the test piece, and only pass fluctuations in the measured eddy current signals, which would correspond to defects or flaws. The use of a high pass filter is an effective solution to these problems, but it also introduces a significant limitation. While brief fluctuations in the measured eddy current signal will pass through the high pass filter relatively unaltered, a significantly long defect, such as those likely to be present on a steel tube or bar, will undoubtedly be distorted. This can affect the accuracy and, in some cases, even the detection of a flaw or defect itself. Additionally, a high pass filter with a cut off frequency low enough to be of use, whether implemented digitally or in an analog circuit, would require significant resources and/or processing time.

A method proposed in U.S. Pat. No. 4,218,651 discloses a method which uses at least one eddy current probe fixed in a test head which allows the probe or probes to revolve around a test piece. This technique, and variations thereof, has become standard practice and should be well-known to those familiar with prior art. Using such a method, a defect parallel to the longitudinal axis of a test piece would be reliably measured even with a high pass filter being used to process the raw measurement data. However, such a method invariably requires a complex mechanical fixture, which will increase the cost and decrease the reliability of the test system and significantly limit the speed at which units can be tested. In addition, such a method is only useful for cylindrical test pieces.

Other related and background art can be found in U.S. Pat. Nos. 3,152,302, 4,203,069, 3,906,357, 4,673,879, 4,965,519, and 5,371,462. The contents of the aforementioned patents are incorporated by reference herein.

Accordingly it would be advantageous to provide a method of processing signals from an eddy current array which eliminated the effects of differing baseline impedances between test pieces and those of baseline drift while not distorting actual defect data. Further, it would be advantageous if this method were mechanically simple to implement and conducive to high scan rates. It would also be advantageous if this new method were applicable to bars with cross sections of geometries other than round, such as, but not limited to, oval, rectangular, and hexagonal. It would also be advantageous if this new method could be implemented without using an exceeding amount of system resources or processing time.

SUMMARY OF THE DISCLOSURE

It is an object of the present disclosure to overcome the problems associated with prior art. The present disclosure does this by replacing the high pass filter of the typical prior art eddy current array system with a system of processing algorithms designed to iteratively eliminate the normal impedance baseline shifts between test pieces without distorting defect readings. Used in concert, three algorithms described below work to eliminate baseline offset sensed by an eddy current probe while still allowing longitudinal defects—defects running along the surface of a test piece parallel to the scan direction—to be measured accurately.

The first of these three algorithms, the Mean Value Analysis Correction (MVAC) algorithm, is used to reduce the range of the baseline offset resulting from the overall average impedance shifts from test piece to test piece and is only useful when using an eddy current array probe. The MVAC algorithm averages the impedance values measured by each of the elements in the eddy current array—excluding those measurements outside a set range which could represent legitimate defects or flaws—and then shifts the raw data readings from each of the elements by this Mean Impedance Value. In the preferred embodiment of the present disclosure, this Mean Impedance Value is calculated once per test piece, and all subsequent measurements on the test piece are shifted by this value. In this way, a coarse adjustment will be made to move the baseline impedance sensed by each element in the eddy current array probe closer to the null point in the impedance plane, thereby significantly reducing the potential baseline shift between test pieces.

The second baseline offset correction algorithm, the Limited Initial Value Correction (LIVC) algorithm, is specifically used to reduce the dispersion of impedance readings sensed from each of the elements in the eddy current array probe. Unlike the MVAC algorithm, the LIVC algorithm is useful for both single element and eddy current array probes. The LIVC algorithm makes use of a pair of operator defined Translation Factors to shift impedance readings closer to the null point in the impedance plane. In the preferred embodiment of the present disclosure, the LIVC algorithm is run once per test piece, and a pair of Translation Parameters defined for each element in the eddy current probe array. These Translation Parameters are then used to adjust all subsequent measurements on the test piece.

The third algorithm, the Bounded Iterative Offset Correction (BIOC) algorithm, is used specifically to combat baseline drift. The BIOC algorithm iteratively adjusts the impedance readings from each measurement toward the null point in the impedance plane using fixed value steps. The value of these adjustment steps, referred to as the Slope Value, is set by a test operator depending on test conditions and is typically selected to be twice the average slope of the anticipated baseline drift. Defect measurements are preserved in the BIOC algorithm by suspending the iterative adjustment whenever the magnitude of a reading is outside the bounds of a preset Threshold Value. This Threshold Value is set by the test operator, depending on test conditions, and is typically set to a value just less than the alarm gates. Like the LIVC algorithm, the BIOC algorithm can be useful for single element as well as array probe systems.

The present disclosure also provides for a series of eddy current probe balancing, or null, algorithms which are specially designed to be conducive with the methods of the present disclosure. These methods, combined with the BIOC, MVAC, and LIVC algorithms, provide for a complete eddy current inspection system optimized for testing for elongated defects running parallel to the scan axis, referred to in the present disclosure as longitudinal defects.

Accordingly, it is an object of the present disclosure to provide a method for processing and interpreting data acquired from an eddy current array probe inspection system which eliminates the problems of baseline offset and baseline drift without compromising the detection of longitudinal defects.

It is also an object of the present disclosure that this method be mechanically simple to implement and require no rotation of the eddy current probe relative to the test piece.

It is further an object of the present disclosure to provide a method for balancing an eddy current array probe in a manner conducive to a system employing these algorithms.

In the preferred embodiment of the present disclosure, a ring shaped eddy current array probe is positioned around a test piece, preferably an elongated bar. The impedance measurements sensed by the individual elements are first shifted by the Mean Impedance Value—determined by the MVAC algorithm—then parametrically shifted again by a set of Translation Parameters—determined by the LIVC algorithm—to correct any baseline offset, then processed through a low pass filter to reduce high frequency noise, and finally adjusted by the BIOC algorithm to continually correct for any baseline drift.

Other features and advantages of the present invention will become apparent from the following description of the invention that refers to the accompanying drawings.

BRIEF DESCRIPTION OF THE DRAWINGS

FIG. 5B is a mathematical representation of the Bounded Iterative Offset Correction (BIOC) algorithm;

DETAILED DESCRIPTION OF EMBODIMENTS OF THE INVENTION

In prior art eddy current inspection systems, a high pass filter is used on raw measurement data to eliminate any DC offset sensed by the elements in the eddy current probe array. This DC offset can come from a variety of sources, such as, but not limited to, temperature variation over the course of testing and metallurgic or geometric differences between test pieces, and can adversely impact the inspection process. A high pass filter is well suited to eliminate this DC offset, however under certain conditions this same filter can distort measurement data and impede the analysis and detection of a defect. Moreover, a significantly long defect on a test piece will be indistinguishable from DC offset to a traditional high pass filter, significantly increasing the likelihood that the defect will not be detected at all. The methods of the present disclosure combine to eliminate the need for this high pass filter.

Figure 1:
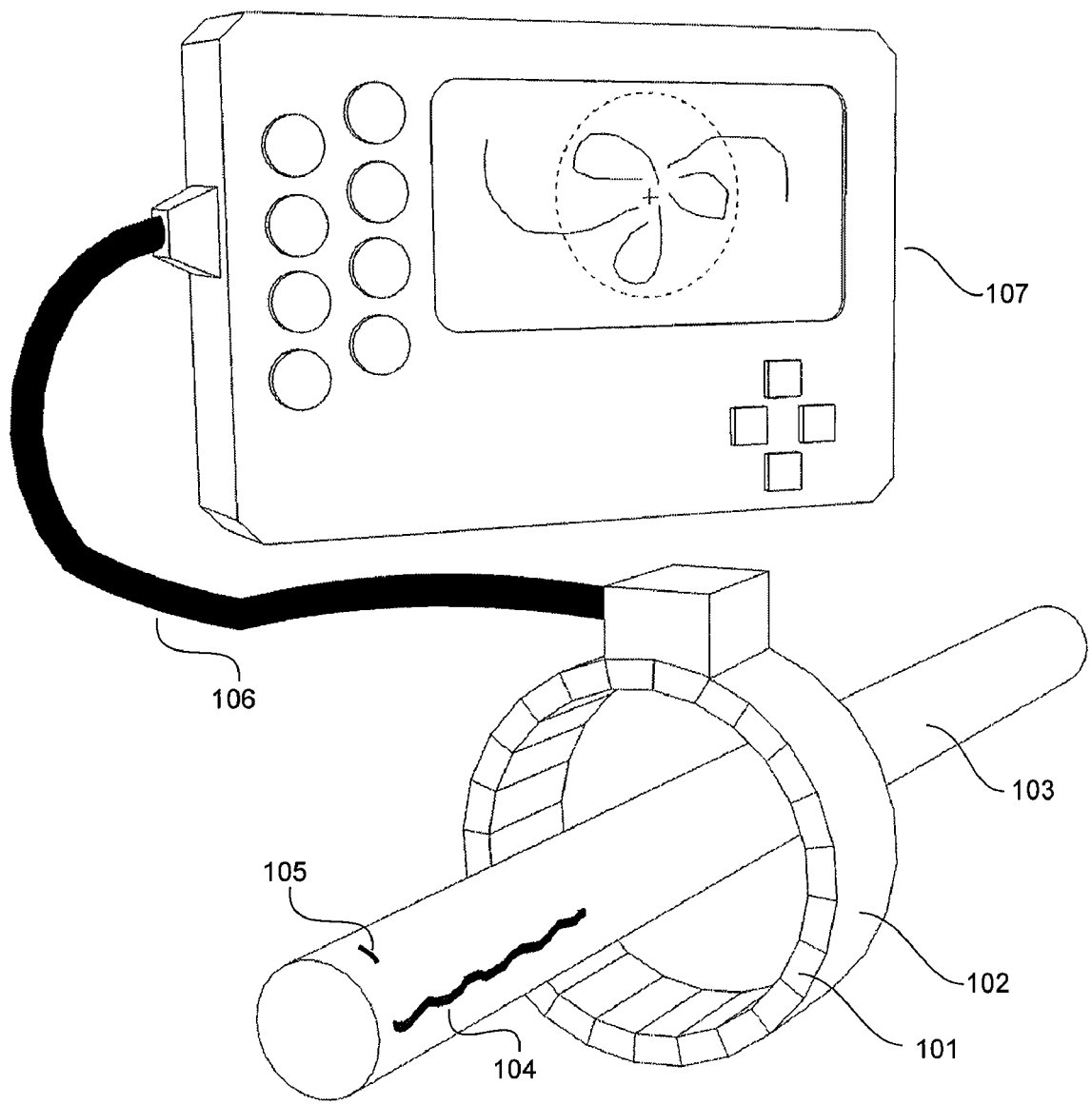
FIG. 1 is a perspective drawing illustrating a typical eddy current array inspection system.

FIG. 1 illustrates a typical eddy current inspection system that would employ the methods of the present disclosure. A plurality of eddy current coils 101 are arranged in a ring shaped array 102 about a test piece 103. The test piece 103 is shown to have two defects. The first defect 105 is a relatively small flaw, oriented perpendicular to the eddy current probe scan direction, and scan data taken over this flaw would likely pass through the high pass filter of prior art eddy current inspection systems without any significant distortion. However, the second defect 104 is significantly long and oriented parallel to the direction of the eddy current probe scan. In the case of this second defect 104, data obtained from scanning would most likely be distorted by the use of a high pass filter.

An interface cable 106 transmits excitation signals from the instrument assembly 107 to the eddy current array 102 as well as measurement signals sensed by the eddy current array 102 back to the instrument assembly 107 where the methods of the present invention will be used to process the received data. Depending on the complexity of the eddy current inspection system, the instrument assembly 107 is typically either a handheld device or PC based system.

Figure 2:
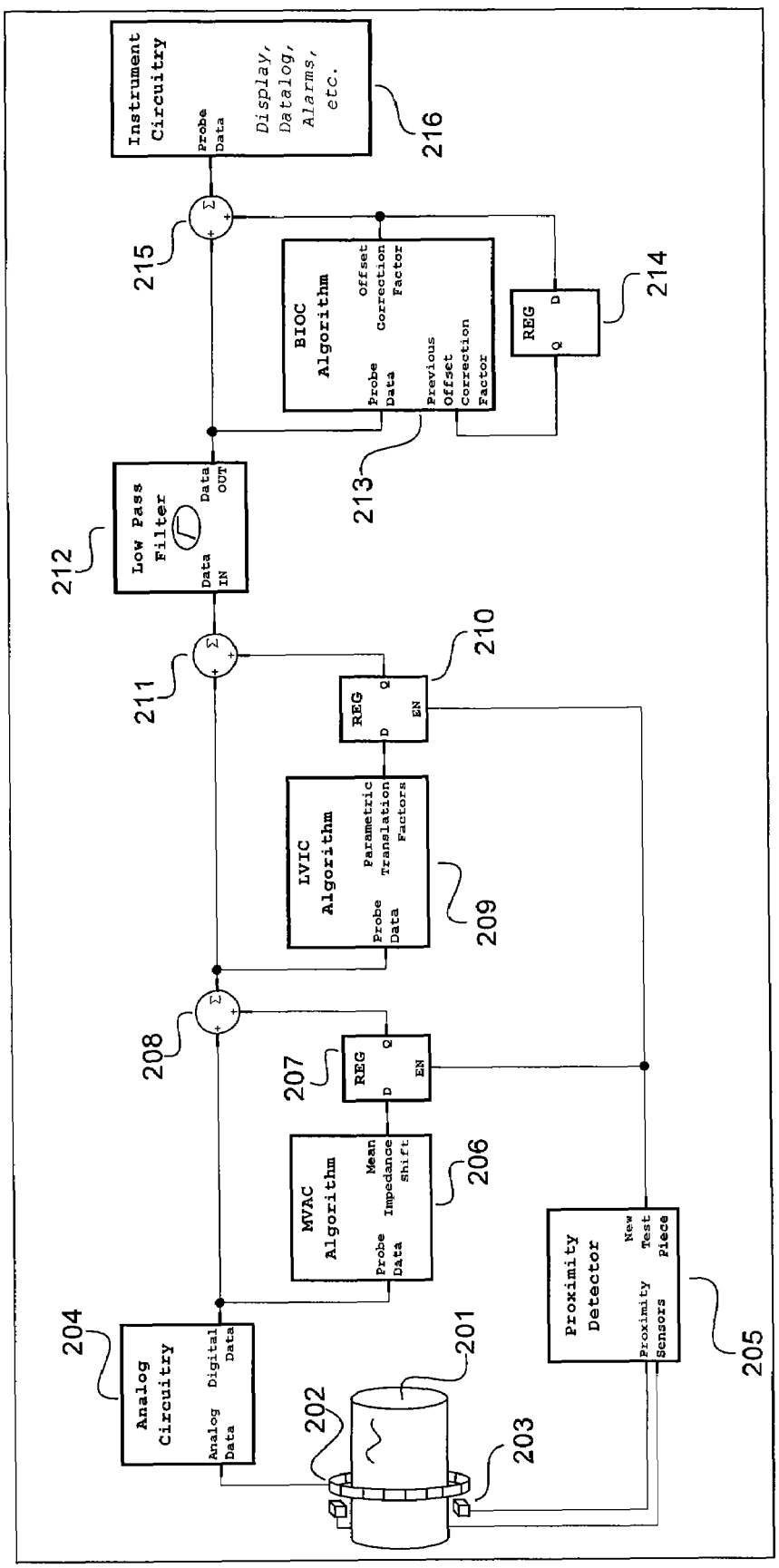
FIG. 2 is a block diagram of the eddy current inspection system of the preferred embodiment of the present disclosure.

FIG. 2 illustrates—through the use of a simplified block diagram—the preferred embodiment of the present disclosure as it would function inside the eddy current inspection system of FIG. 1. Although the following discussion of the present disclosure speaks specifically to the implementation detailed in FIG. 2, the present disclosure is not limited in this regard. The methods of the present disclosure are applicable to other implementation schemes including, but not limited to, an implementation without a low pass filter 212 and an implementation where the MVAC algorithm 206 is run more than once per test piece 201. The methods of the present invention are also applicable to other eddy current probe array configurations, such as, but not limited to, linear, wedge, and rectangular and other test objects, such as, but not limited to, pipe welds, metal plates, and shaped coupling pieces.

Test signals received from the eddy current array probe 202 as it scans the test piece 201 are processed and digitized through analog circuitry 204. Numerous methods for processing and digitizing the raw analog signals from the eddy current array probe 202 are well-known to those familiar with the art and are not specific to the methods of the present disclosure. The proximity sensors 203 detect the leading edge of a new test piece and alert the proximity detector block 205. The proximity detector block will then enable new adjustment parameters from the MVAC algorithm block 206 and the LIVC algorithm block 209 to be loaded in the registers 207 and 210, respectively.

The MVAC algorithm block 206 makes a coarse measurement of the baseline impedance of the new test piece, and this value—referred to in the present disclosure as the Mean Impedance Shift Value—is used to shift every subsequent data point, compensating for the overall average impedance change present on the new test piece. The LIVC algorithm block 209 calculates a set of Translation Parameters for each element in eddy current probe array 202, and these values are used to adjust each subsequent reading, significantly reducing the dispersion of measurement readings between the different elements of the eddy current probe array. The MVAC algorithm 206 and the LIVC algorithm 209 and the relevance of the Mean Impedance Shift Value and LIVC Translation Parameters are discussed in detail in subsequent sections below.

Digitized data is passed through a low pass filter block 212 to eliminate any high frequency noise sensed by the eddy current array probe 202. The filtered data is then adjusted by the Offset Correction Factor calculated by the BIOC algorithm 213. The BIOC algorithm 213 iteratively adjusts the baseline impedance of the test piece 201 (as sensed by the eddy current array probe 202) to the null point in the impedance plane. To prevent distortion of potential defect data, this iterative adjustment process is suspended when data readings exceed a specified threshold. The BIOC algorithm 213 and the calculation of the correction factor are discussed in detail in a subsequent section below.

Once corrected by the BIOC algorithm 213, the adjusted probe data is passed on to the instrument circuitry 216 where it can be analyzed by other digital signal processing algorithms, displayed to the user, stored for later analysis, or checked against alarm algorithms.

MVAC Algorithm

A significant source of overall baseline impedance variation between test pieces comes from metallurgic and geometric variations among the test pieces themselves. Even in an ideal case where an eddy current array inspection system were perfectly calibrated and balanced using a precise standard or golden unit prior to testing, variations in the manufacturing process or ambient temperature changes, for example, would undoubtedly result in differences in the baseline impedance sensed by the eddy current probes. These unavoidable impedance differences represent a significant hindrance to the sensitivity of the eddy current inspection system, and therefore, an algorithm is required to minimize these overall average impedance shifts at the beginning of each new test piece.

Figure 3:
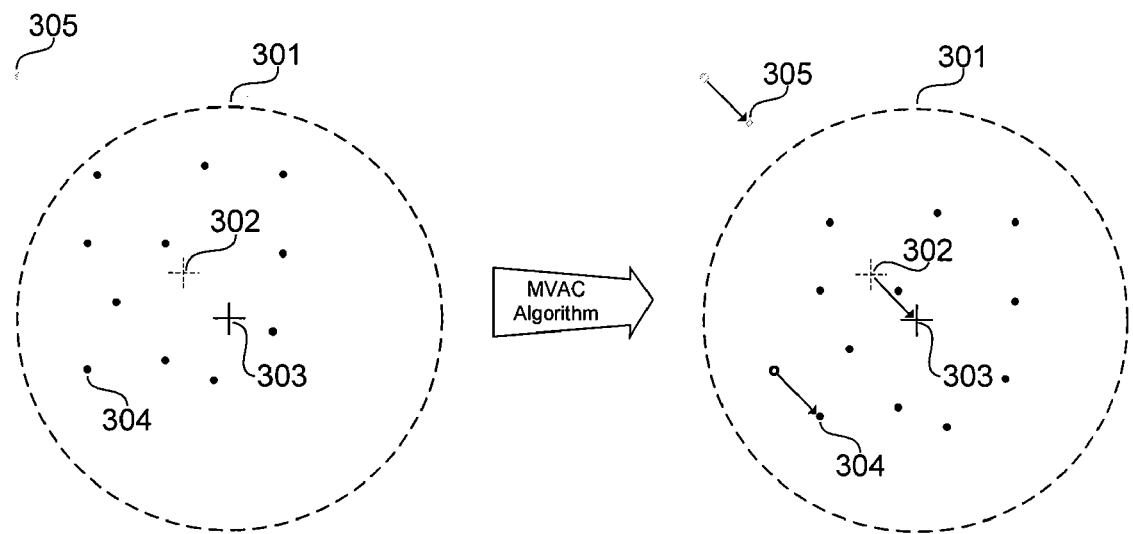
FIG. 3 is a graphical representation of the Mean Value Analysis Correction (MVAC) algorithm.

FIG. 3 illustrates this new algorithm, referred to in the present disclosure as the Mean Value Analysis Correction (MVAC) algorithm. When a new test piece is detected by the eddy current inspection system's proximity sensor, the impedance measurements from each of the elements in the eddy current probe array are averaged to calculate the baseline impedance value—represented by the dashed cross 302—of the new test piece. To prevent any defects in the test piece or damaged array elements from erroneously shifting this calculated value, only those readings which fall within a predetermined range—represented by the dashed circle 301—are included in the calculation. The black circles 304 represent readings used in this calculation. The grey circle 305 represents a possible defect or otherwise bad reading and is removed from the calculation.

A Mean Impedance Shift Value is calculated—by taking either the mean or the median of the valid impedance readings—representing the delta between the calculated baseline impedance value 302 and the "null point" in the impedance plane, represented by the solid cross 303. All subsequent measurements made on the test piece—including those outside the predetermined range 301—are then shifted by this delta value for the remainder of the test scan. As can be seen from FIG. 3, this shift significantly reduces the baseline impedance offset of the new test piece.

LIVC Algorithm

Figure 4A:
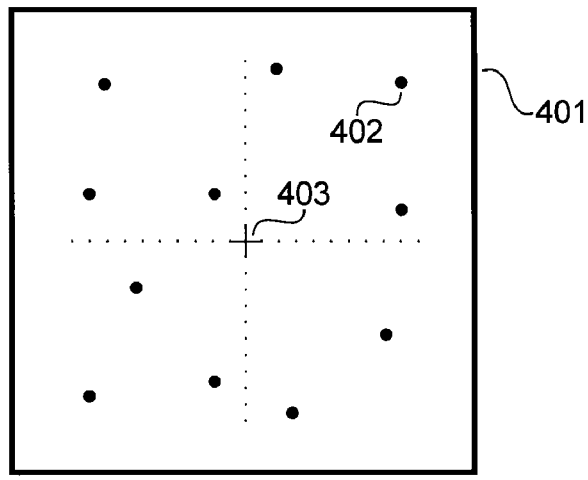
FIGS. 4A-4C are graphical representations of the Limited Initial Value Correction (LIVC) algorithm.
Figure 4B:
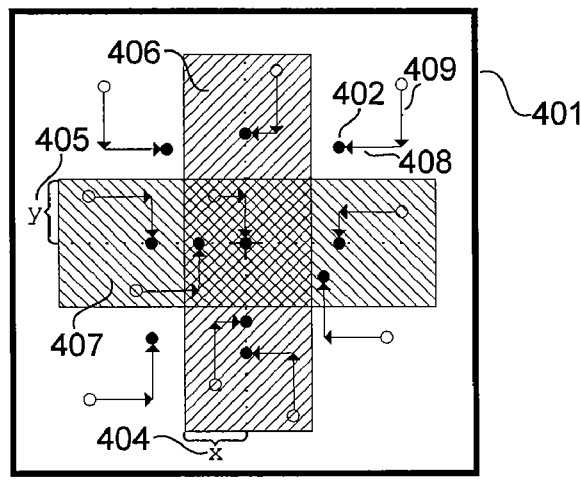
Figure 4C:
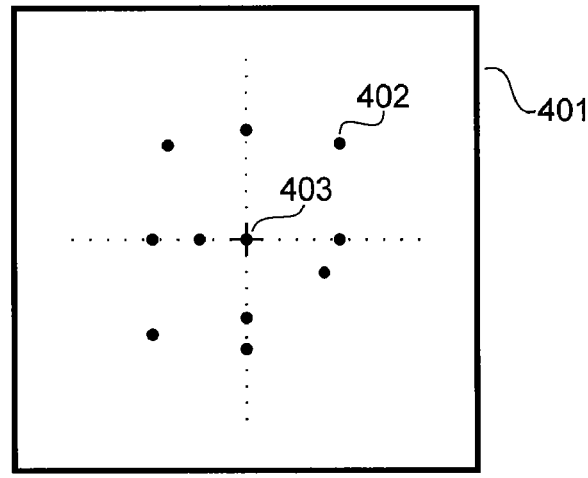

As can be seen from FIG. 3, the MVAC algorithm is an effective means of shifting the overall average impedance sensed by the elements of the eddy current probe array to the null point in the impedance plane 303. However, the individual impedance readings 304 from each element are still widely dispersed about the null point 303. This dispersion is a result of the localized metallurgic and geometric variations sensed by each of the individual elements in the eddy current probe. An algorithm is required to adjust for these offset variations between test pieces on an individual element basis. FIGS. 4A-4C illustrate just such an algorithm: the Limited Initial Value Correction (LIVC) algorithm. Working in concert with the MVAC algorithm, the LIVC algorithm can be used to further reduce the baseline offset of the eddy current measurement data by minimizing measurement dispersion in the impedance plane.

FIG. 4A represents measurement data that has been processed by the MVAC algorithm. Each of the black circles 402 in the impedance plane 401 represents an impedance measurement from an element in the eddy current probe array. The adjustments made by the MVAC algorithm have ensured that the impedance readings are generally centered about the null point 403, however there is still a significant amount of dispersion among the measurement readings 402.

FIG. 4B illustrates the application of the LIVC algorithm. A pair of Translation Factors, termed X 404 and Y 405, is set by the test operator. As can be seen from FIG. 4B, the X Translation Factor 404 defines a rectangular area 406 in the impedance plane 401 symmetric about the vertical axis, and the Y Translation Factor 405 defines a similar area 407 symmetric about the horizontal axis. The Translation Factors are used to parametrically adjust each of the impedance readings 402 and define a set of Translation Parameters—represented by the arrows 408 and 409—for each element in the eddy current probe array. Measurements falling outside of both shaded areas 406 and 407 are shifted toward the null point 403 in both the horizontal and vertical directions by the X 404 and Y 405 Translation factors respectively. Measurements falling inside the horizontal shaded area 407 but not the vertical shaded area 406 are shifted to the horizontal axis in the vertical direction and toward the null point by the X Translation Factor 404 in the horizontal direction. Likewise, measurements falling inside the vertical shaded area 406 but not the horizontal shaded area 407 are shifted to the vertical axis in the horizontal direction and toward the null point by the Y Translation Factor 405 in the vertical direction. Finally, measurements falling inside both the horizontal shaded area 407 and the vertical shaded area 406 are shifted exactly to the null point 403. The magnitude and direction of each shift—unique for each element in the eddy current probe array—are defined as the Translation Parameters for each element and, again, best represented by the arrows 408 and 409. In the preferred embodiment of the present disclosure, the LIVC algorithm is run once per test piece, the entire set of Translation Parameters for the eddy current probe array stored, and all subsequent readings adjusted by those parameters for the remainder of the test scan.

FIG. 4C represents measurement data after it has been adjusted by the LIVC Translation Parameters. Measurement readings 402 are still centered about the null point 403, but are now grouped tighter around that point, significantly reducing baseline offset.

BIOC Algorithm

The MVAC and LIVC algorithms work in concert to correct for any baseline impedance variation between different test pieces in an eddy current array inspection system. However they do nothing to correct for impedance variations seen along the scan axis of individual test pieces. Impedance non-homogeneity along the scan axis of a test piece can result in a phenomena typically referred to as baseline drift, where the baseline impedance sensed by an eddy current probe tends to drift within the impedance plane over the course of the scan. Without a high pass filter in the system to correct this, a new algorithm is required to specifically target baseline drift.

The Bounded Iterative Offset Correction (BIOC) algorithm is implemented by driving the data signal sensed from each of the elements in the eddy current probe array toward the baseline, or null point, in the impedance plane in relatively small, iterative steps defined by a constant, predetermined Slope Value. For measurements whose magnitudes are greater than a predetermined Threshold Value—thus indicating a potential defect—this driving adjustment is suspended to preserve the measurement data. The Slope Value is typically chosen to be twice the average slope of the anticipated baseline drift. This would be a value well-known to a test operator for a given test setup and would typically be determined empirically when an eddy current inspection system was first installed. The Threshold Value is typically chosen to be a value just less than the alarm setting to provide some hysteresis between readings which are considered baseline drift errors and those which are considered legitimate defects. Again, the required delta between the Threshold Value and the alarm setting would be typically determined empirically when an eddy current inspection system was first installed. The use of a low pass filter (as shown in FIG. 2) can significantly reduce the required delta between the Threshold Value and the alarm setting by eliminating or greatly reducing the high frequency noise on the measurement signal.

Figure 5A:
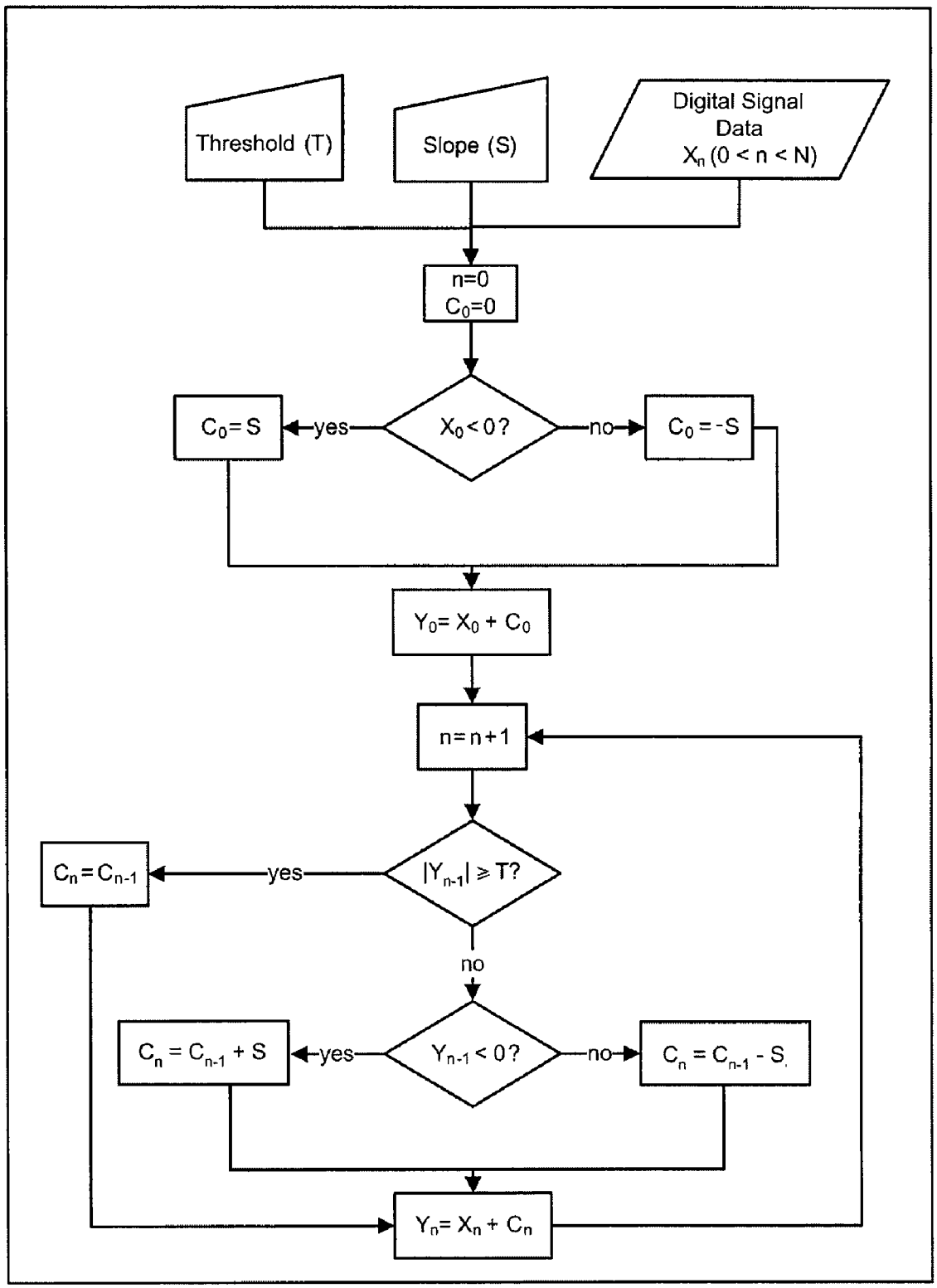
FIG. 5A is a flow chart illustrating the Bounded Iterative Offset Correction (BIOC) algorithm.

FIG. 5A presents the BIOC algorithm in the form of a flow chart while FIG. 5B presents the same in mathematical terms. Either or both of these figures should be used to aid the following detailed discussion of the BIOC algorithm.

After every measurement, a correction factor ($C_n$) is added to the raw data point ($X_n$) to produce a corrected value ($Y_n$). On the first cycle of the algorithm (n=0) the correction factor ($C_0$) is initialized based on the sign of the first raw data point ($X_0$). If the first raw data point ($X_0$) is positive, representing a reading above the baseline or in the upper two quadrants of the impedance plane, the correction factor ($C_0$) is initialized to the negated preset Slope Value (−S). If the first raw data point ($X_0$) is negative, representing a reading below the baseline or in the lower two quadrants of the impedance plane, the correction factor ($C_0$) is initialized to the preset Slope Value (S).

Under normal conditions—when the magnitude of the previous corrected value ($Y_{n-1}$) is within the set threshold range—the correction factor ($C_n$) is adjusted each time before it is added to the raw data point ($X_n$). This adjustment is based on the sign of the previous corrected value ($Y_{n-1}$). If the previous corrected value ($Y_{n-1}$) was positive, representing a reading above the baseline or in the upper two quadrants of the impedance plane, the correction factor ($C_n$) is decreased by the slope value. If the previous corrected value ($Y_{n-1}$) was negative, representing a reading below the baseline or in the lower two quadrants of the impedance plane, the correction factor ($C_n$) is increased by the slope value. In this way, any signal drift, either positive or negative, sensed by the eddy current probe will be canceled out over the course of the first several measurements.

Contrary to this normal operation, when the magnitude of the previous corrected value ($Y_{n-1}$) is outside the set threshold range—most likely indicating a defect in the test piece—no adjustment to the correction factor ($C_n$) is made, and the previous correction factor value ($C_{n-1}$) is used. In this way the correction algorithm will preserve any potential defect data while still maintaining DC offset compensation.

Figure 6:
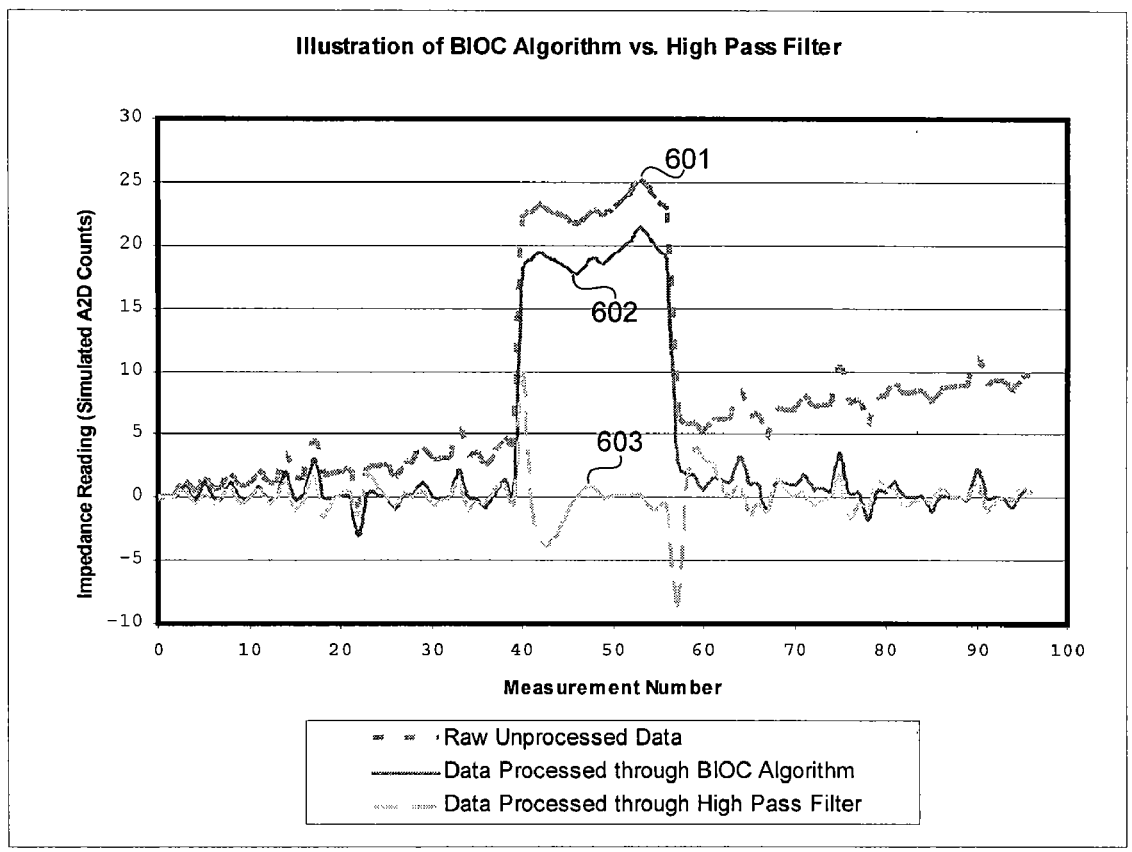
FIG. 6 is a graph comparing the effect of the Bounded Iterative Offset Correction (BIOC) algorithm to that of a typical high pass filter on simulated raw data.

FIG. 6 graphically illustrates the function of the BIOC algorithm by plotting simulated impedance readings as one dimensional scalar values (the vertical component of the signal from a single element in the eddy current probe array). The short dashed curve 601 represents raw, uncorrected data showing a steady and constant baseline drift (about 0.1 counts per measurement). The solid curve 602 represents the simulated data corrected using the BIOC algorithm. For the first forty measurements, the baseline drift is compensated for, and the baseline impedance is held around zero and remains there until a flaw is detected. At that point (at measurement #40) the offset correction adjustment value is held constant, and no alteration is made to the defect data measurements, as can be observed by comparing the shape of the solid curve 602 to that of the short dashed curve 601 between measurements #40 and #58. Note that once the defect has passed, the iterative adjustments to the correction value resume, and the baseline offset quickly returns to zero. For comparison, the long dashed curve 603 represents the simulated data processed through a typical high pass filter. The baseline drift is eliminated, but the defect data between measurements #40 and #58 is significantly distorted.

Eddy Current Array Probe Balancing

The MVAC, LIVC, and BIOC algorithms disclosed in previous sections work to correct baseline offsets associated with impedance changes between or along test pieces. However, all three of these algorithms require that the eddy current test probe be reasonably balanced before testing begins such that any significant baseline offsets sensed by the eddy current probe can be known to come only from test piece impedance variation. Given this, it is reasonable to assume that an eddy current test system employing the algorithms of the present disclosure would require more accurate probe balancing than prior art systems. To provide for this, the following three eddy current probe balancing algorithms are disclosed, which are simple to execute and can be performed with test pieces of unknown quality.

Figure 7A:
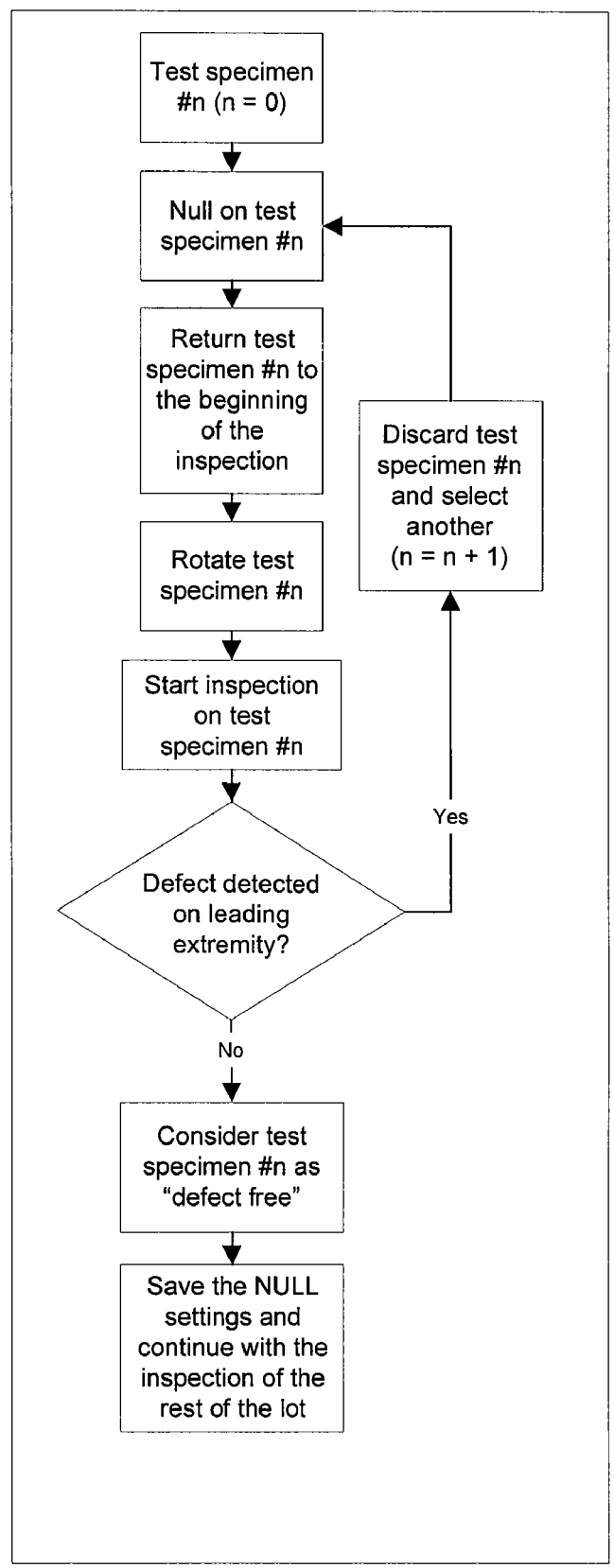
FIGS. 7A-7C are flow charts illustrating the three balancing algorithms of the present disclosure.
Figure 7B:
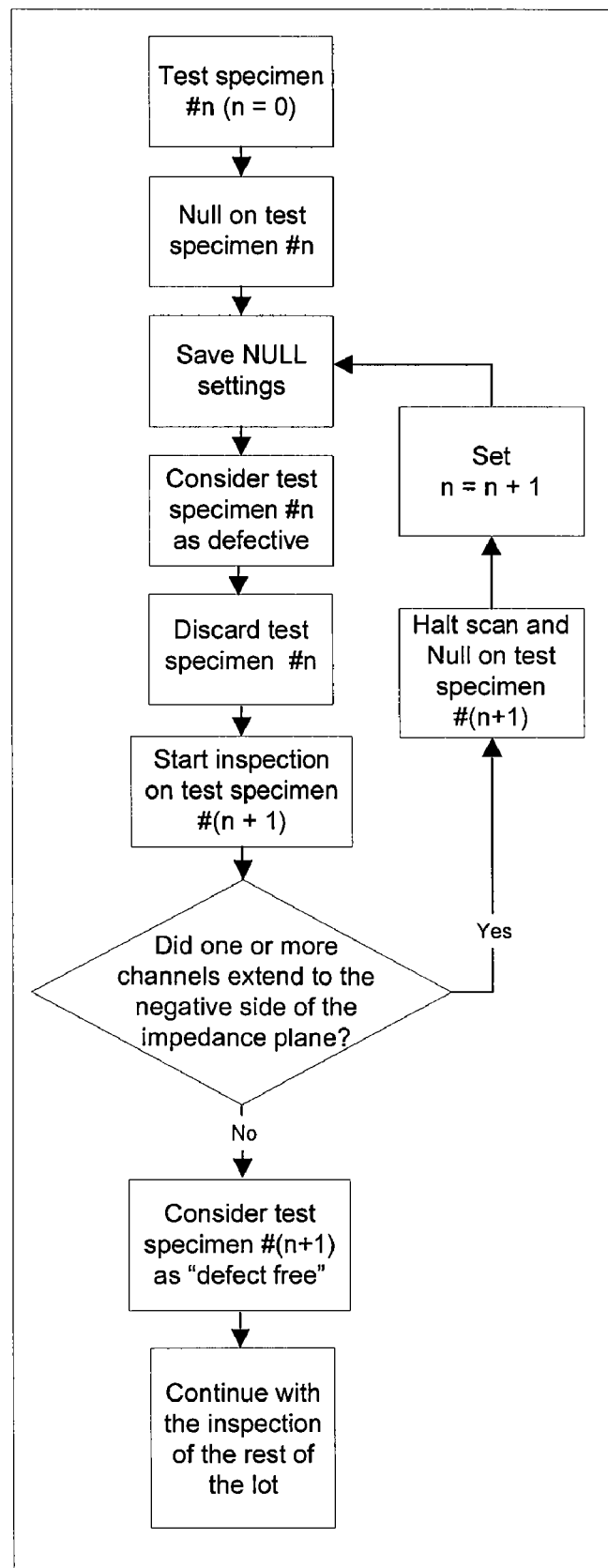
Figure 7C:
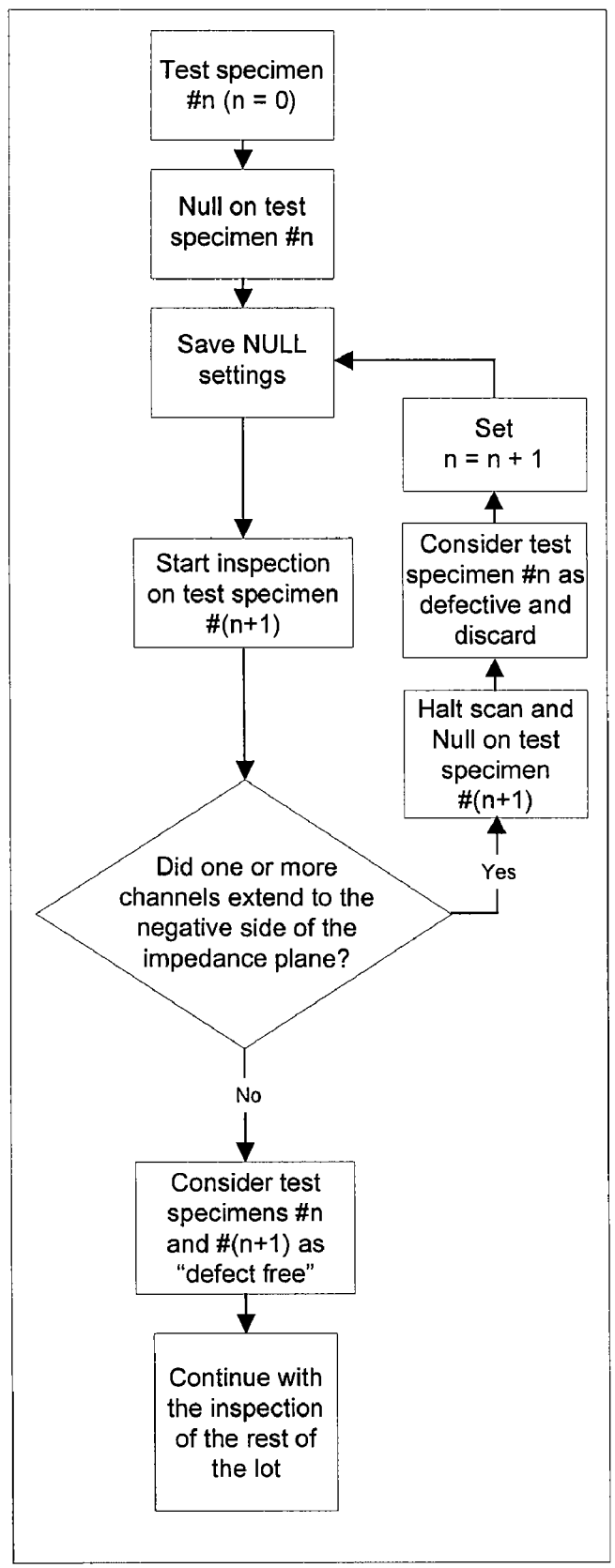

FIGS. 7A-7C illustrate three eddy current probe balancing, or NULL, algorithms through a series of flow charts. All three algorithms balance an eddy current array probe without the need for an ideal measurement standard or golden unit, and as such can be conveniently run much more often than prior art balancing algorithms. For the following discussion, it is assumed that the eddy current test system has been first calibrated such that any actual defect—that is a legitimate physical defect on a test piece and not an erroneous artifact of improper probe balancing—will appear in the positive half of the impedance plane. Such a calibration process should be well-known to those skilled the art. With such a setup, the positive envelope of the signal can be used for defect detection, and its negative equivalent can be used for eddy current array probe balance quality validation.

The first method, illustrated in FIG. 7A, is useful in a test situation in which it is possible and convenient to scan and rotate one test piece several times in a row. The elements of the eddy current array are initially balanced using a test piece of undetermined quality. The same test piece is then returned to the start of the inspection process and rotated. The degree of rotation is arbitrary so long as the individual eddy current array elements inspect a section of the test piece different than during the first inspection. If an elongated defect is detected during the second inspection in the balancing zone on the leading extremity, the test specimen is discarded and the process is repeated with the next test specimen until there is no defect detected in the balancing zone.

The second method, illustrated in FIG. 7B, is useful in a test situation in which a test piece may only be tested once, and a decision as to the quality of the test piece must be made immediately after its first and only test scan. The elements of the eddy current array are initially balanced using a first test piece of undetermined quality. This first test piece is then considered defective and discarded to the failure bin. A second test piece is then inspected. If the scan of the second test piece is completed without any of the elements of the eddy current probe array providing an output which extends into the negative half of the impedance plane, then the second test piece is considered passed, and the eddy current probe considered balanced. However, if any of the probe array measurements do extend into the negative half of the impedance plane, it is assumed that improper balancing has occurred on the first test piece. Scanning of the second test piece is halted, and the elements of the eddy current array are rebalanced (using the second test piece). The second piece is then considered defective and discarded to the failure bin. A third test piece is then chosen and the validation scan process repeated. The cycle continues until a test piece is scanned, after a balancing cycle, without any of the elements of the eddy current probe array producing a negative measurement.

The third method, illustrated in FIG. 7C, is useful in a test situation in which a test piece may only be tested once, but a decision as to the quality of the test piece may be postponed until a second test piece has been scanned. The elements of the eddy current array are initially balanced using a first test piece of undetermined quality. This first test piece is then set aside, and a second test piece is inspected. If the scan of the second test piece is completed without any of the elements of the eddy current probe array providing an output which extends into the negative half of the impedance plane, then both the first and the second test pieces are considered passed, and the eddy current probe considered balanced. However, if any of the probe array measurements do extend into the negative half of the impedance plane, it is assumed that improper balancing has occurred on the first test piece. Scanning of the second test piece is halted, and the elements of the eddy current array are rebalanced (using the second test piece). The first test piece is then considered defective and discarded to the failure bin, and the second piece is set aside. A third test piece is then chosen and the validation scan process repeated. The cycle continues until a test piece is scanned, after a balancing cycle, without any of the elements of the eddy current probe array producing a negative measurement.

Although the present invention has been described in relation to particular embodiments thereof, many other variations and modifications and other uses will become apparent to those skilled in the art. It is preferred, therefore, that the present invention not be limited by the specific disclosure herein.

What is claimed is:

1. An eddy current flaw detection system, comprising:
   an eddy current array probe for inducing eddy currents in a test object and for obtaining eddy current data from the test object;
   a processing system for processing the eddy current data; and
   a display system for displaying test results for the test object;
   wherein the processing system comprises a bounded iterative offset correction (BIOC) facility which is structured to reduce baseline drift by iteratively adjusting impedance readings from various measurements toward a null point in an impedance plane.

2. The system of claim 1, further including a mean value analysis correction (MVAC) facility that is structured to reduce the range of baseline offsets resulting from average impedance shifts from test object to test object.

3. The system of claim 1, further including a limited initial value correction (LIVC) facility which is structured to reduce the dispersion of impedance readings sensed from various ones of sensing elements which comprise the eddy current array probe.

4. The system of claim 1, including a low pass filter disposed before the BIOC facility.

5. The system of claim 1, wherein the BIOC facility is structured to reserve potential defect data while maintaining DC offset compensation.

6. The system of claim 1, further including a proximity detector that senses when the eddy current array probe is within a predefined distance to the test object and for synchronizing the MVAC and LIVC algorithms.

7. The system of claim 1, wherein the MVAC facility is structured to exclude measurements obtained from the MVAC facility which lie outside a set range of values which is associated with legitimate defects or flaws.

8. The system of claim 1, in which the MVAC facility is structured to develop one of the mean and the median imped ance value which is calculated once per test object, and utilized subsequently in the scanning of the test object.

9. The system of claim 1, in which the LIVC facility is structured to utilize operator defined translation factors to shift impedance readings closer to a null point in an impedance plane.

10. The system of claim 9, wherein the translation factors include a pair of factors associated, respectively, to x and y directions.

11. The system of claim 9, wherein the translation factors include a fixed vector.

* * * * *